United States Patent
Jenkins et al.

(10) Patent No.: US 8,909,320 B2
(45) Date of Patent: Dec. 9, 2014

(54) CABLE MANAGEMENT SYSTEMS FOR MRI SYSTEMS AND RELATED METHODS

(75) Inventors: Kimble Jenkins, Memphis, TN (US); Kamal Vij, Chandler, AZ (US); Peter Piferi, Orange, CA (US)

(73) Assignee: MRI Interventions, Inc., Memphis, TN (US)

( * ) Notice: Subject to any disclaimer, the term of this patent is extended or adjusted under 35 U.S.C. 154(b) by 1192 days.

(21) Appl. No.: 12/708,773

(22) Filed: Feb. 19, 2010

(65) Prior Publication Data

US 2010/0217113 A1 Aug. 26, 2010

Related U.S. Application Data

(60) Provisional application No. 61/154,254, filed on Feb. 20, 2009.

(51) Int. Cl.
| | |
|---|---|
| A61B 5/05 | (2006.01) |
| G01R 33/28 | (2006.01) |
| A61B 5/00 | (2006.01) |
| H02G 11/00 | (2006.01) |
| A61N 1/08 | (2006.01) |
| A61B 5/0428 | (2006.01) |

(52) U.S. Cl.
CPC ........... G01R 33/28 (2013.01); A61N 2001/086 (2013.01); A61B 2562/222 (2013.01); A61B 5/0002 (2013.01); A61B 5/04286 (2013.01); A61B 5/0006 (2013.01); H02G 11/00 (2013.01)
USPC ........... 600/411; 600/407; 600/410; 600/421; 5/600; 5/601

(58) Field of Classification Search
USPC ............... 600/407, 410, 411, 421; 5/600, 601
See application file for complete search history.

(56) References Cited

U.S. PATENT DOCUMENTS

| | | | | |
|---|---|---|---|---|
| 3,931,452 | A | * | 1/1976 | Nilsson .......................... 174/491 |
| 4,972,852 | A | * | 11/1990 | Koob et al. .................... 600/415 |
| 5,442,858 | A | | 8/1995 | Wolters et al. |
| 5,464,014 | A | * | 11/1995 | Sugahara ...................... 600/411 |
| 6,202,360 | B1 | | 3/2001 | Rattner et al. |
| 6,675,720 | B2 | * | 1/2004 | Peterson et al. .............. 104/196 |
| 7,561,906 | B2 | | 7/2009 | Atalar et al. |

(Continued)

FOREIGN PATENT DOCUMENTS

| | | |
|---|---|---|
| DE | 10103794 | 8/2002 |
| EP | 0487441 | 5/1992 |
| JP | 3001842 | 1/1991 |

OTHER PUBLICATIONS

International Search Report and Written Opinion for corresponding PCT Application No. PCT/US2010/000482, Date of mailing Aug. 27, 2010.

(Continued)

Primary Examiner — Tse Chen
Assistant Examiner — Jason Ip
(74) Attorney, Agent, or Firm — Myers Bigel Sibley & Sajovec, P.A.

(57) ABSTRACT

The disclosure describes cable management systems that provide adjustable lengths of cables that connect to various electronic medical or surgical tools. The systems can reduce the lengths of loose or hanging cables and define routes that preventing cross-over, looping and/or bunching of loose lengths of long cables.

25 Claims, 10 Drawing Sheets

(56) References Cited

U.S. PATENT DOCUMENTS

| | | | |
|---|---|---|---|
| 2003/0033675 A1 | 2/2003 | Solesbee et al. | |
| 2004/0116800 A1* | 6/2004 | Helfer et al. | 600/411 |
| 2004/0237202 A1 | 12/2004 | Gallant et al. | |
| 2006/0273211 A1* | 12/2006 | Langberg et al. | 242/388.91 |
| 2008/0243218 A1 | 10/2008 | Bottomley et al. | |
| 2008/0262584 A1 | 10/2008 | Bottomley et al. | |
| 2009/0171421 A1 | 7/2009 | Atalar et al. | |

OTHER PUBLICATIONS

Ratnayaka, Kanishka et al., Interventional cardiovascular magnetic resonance: still tantalizing, Journal of Cardiovascular Magnetic Resonance, 2008, 10:62 (23 pages).

The Prucka Cardio Lab 7000®, Product listing and Product photo, http://www.gehealthcare.com/inen/cardiology/invasive/electro_lab/cardiolab_info.html, (2 pages), date unknown but believed to be prior to Feb. 20, 2009 for the purposes of examination.

* cited by examiner

TRACKING COIL FILTERS

FILTERS

DUAL LINE LOW PASS "PI" FILTER

DUAL LINE LATTICE FILTER

CABLE MANAGEMENT SYSTEMS FOR MRI SYSTEMS AND RELATED METHODS

RELATED APPLICATIONS

The application claims priority to and the benefit of priority of U.S. Provisional Application Ser. No. 61/154,254, filed Feb. 20, 2009, the contents of which are hereby incorporated by reference as if recited in full herein.

FIELD OF THE INVENTION

The present invention relates generally to medical devices used during medical procedures and may be particularly suitable for surgical suites for MRI-guided interventional procedures.

BACKGROUND OF THE INVENTION

Some medical and surgical procedures use interventional or monitoring devices with relatively long lengths of various "loose" cables to connect to different electronic power and control systems during the procedures.

SUMMARY OF EMBODIMENTS OF THE INVENTION

Embodiments of the invention may reduce lengths of loose cables and/or tubes conventionally used in medical procedures.

Embodiments of the invention are directed to cable management systems for CT surgical rooms and/or MRI Suites that allow intact patient connection with longitudinal movement of the patient in and out of a magnet bore.

Some embodiments include surgical systems with ceiling and/or floor routed cable paths that can allow take-up of excess lengths of cable and extensions of cable in response to movement of a patient in and out of a scanner bore while providing intact connection of the cables both on a patient end in a patient room of the MRI suite and a workstation end in a different room of the suite.

Some embodiments are directed to cardiac electrophysiology (EP) surgical rooms with an integrated cable management system that houses at least a portion of the cables in a ceiling in the surgical room and slidably extends and retracts the cables into and out of the ceiling while the cables reside entirely above the floor and are adjustable in length to allow a patient to be moved inside the room while the cables remain attached to the components in contact with the patient.

Other embodiments are directed to surgical/diagnostic rooms that include: (a) a patient support table; (b) at least one patch bay of connectors extending along a long side of the table; (c) at least one programmable switch in communication with at least one of the connectors of the at least one patch bay; and (d) a cable management system having at least one cable having a length configured so that a portion of the cable resides in a ceiling associated with the surgical room. The cable management system is configured to extend and retract the at least one cable to allow the at least one cable to have adjustable length and remain connected to the at least one patch bay as the table is moved inside the surgical room.

Yet other embodiments are directed to MRI surgical suites with an integrated cable management system that routes cables from components in contact with a patient to a patch panel using a cable management system that holds at least a portion of the cables in a ceiling of a room with the MR scanner. The cable management system extends and retracts lengths of the cable from the ceiling to allow a patient to be moved longitudinally on a patient table in and out of a magnet bore of the MRI scanner while the cables remain attached to the components in contact with the patient.

Still other embodiments are directed to cardiac EP interventional surgical systems that include: (a) a mat having electrical paths; (b) a plurality of cables in communication with the mat, the cables extending upwardly to reside in a ceiling with a cable management system that extends and retracts the cables to provide adjustable lengths and allow a patient to be moved longitudinally in and out of a magnet bore of an MRI scanner on a scanner table while the cables remain attached to the mat.

In some embodiments, the mat body can reside on a scanner bed under a patient. The mat body has a perimeter and the at least one hub/bay of electrical connectors on long side and/or a foot end portion thereof.

Some embodiments are directed to systems for an MRI diagnostic or interventional procedure. The systems include: (a) a patient support table; (b) at least one patch bay of connectors extending along at least one side of the table; (c) a plurality of first leads, at least one that extends from at least one of the patch bay connectors to an external patient sensor and at least one that extends to an intrabody device; (d) a plurality of second leads having opposing first and second ends, the first ends of the leads connected to the at least one patch bay in communication with a respective one or more the first leads via the at least patch bay, wherein the plurality of second leads are held in at least one cable bundle and the cable bundle extends away from the patch bay with the second ends attached to a patch panel associated with an MRI suite; and (e) a cable management system in communication with the at least one cable bundle, wherein the cable management system is configured to extend and retract the at least one cable bundle to provide an adjustable length of the cable bundle in an MR scanner room whereby the cable bundle is held suspended above the patient and the second leads remain connected to the at least one patch bay and the patch panel as the patient support table is moved a longitudinal distance in and out of a bore of a magnet associated with an MRI scanner.

Still other embodiments are directed to MRI cardiac EP interventional systems that include a magnet room with (i) an MR magnet with a patient support table; (ii) at least one patch bay of connectors extending along a long side of the table; (iii) a plurality of ECG sensors positioned on and/or in a patient, the ECG sensors having leads attached to the at least one patch bay; (iv) at least one intrabody catheter in the patient and being in electrical communication with the at least one patch bay; and (v) a cable management system having cables with opposing first and second ends. The cable management system is configured so that a portion of the cables are supported by a ceiling associated with the magnet room. The cable management system is configured to extend and retract the cables to allow the cables to have adjustable length and to allow the first ends to remain connected to the at least one patch bay as the patient table is moved in and out of a bore of the magnet inside the magnet room. The systems also include a control (scanner) room located adjacent the magnet room and separated by an RF shield with a patch panel in communication with the cables. The control room can include at least one cardiac surgical device including an ECG monitor, an RF generator, an internal defibrillator, an external defibrillator, a cardiac pacer, and a workstation with a display. The at least one cardiac surgical device is in communication with the patch panel to engage a respective cable that connects to a corresponding patient end catheter or sensor.

Still other embodiments are directed to methods of performing CT or MR guided cardiac EP. The methods include: (a) providing a table with at least one patch bay of connections; (b) inserting at least one intrabody (optionally, interventional) device into the patient; (c) positioning ECG sensors on and/or in the patient; (d) connecting leads attached to the intrabody devices and sensors to the at least one patch bay; (e) attaching cables to the at least one patch bay to electrically connect the intrabody catheter and the sensors to remote monitoring and/or control components; and (f) extending and retracting lengths of the cables from a ceiling cable management system in response to moving the patient on the table longitudinally while maintaining the electrical connections between the intrabody catheters and sensors and the remote components.

The steps can be carried out in an MRI suite and the remote components can be located in a scanner control room while the cable management system is located in a magnet room.

Embodiments of the invention provide electrical paths that may reduce problems associated with conventional loose cables and/or tubes used during a medical procedure. The systems can help control the orientation and routing of electrical leads and/or cables used during a medical procedure to reduce "kinking" and/or electrical shorts from same, fluid in connectors and tangling of loose cables, and/or improve patient transportability.

Further features, advantages and details of the present invention will be appreciated by those of ordinary skill in the art from a reading of the figures and the detailed description of the preferred embodiments that follow, such description being merely illustrative of the present invention. Features described with respect with one embodiment can be incorporated with other embodiments although not specifically discussed therewith. Thus, it is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

DETAILED DESCRIPTION OF EMBODIMENTS OF THE INVENTION

Figure 1:
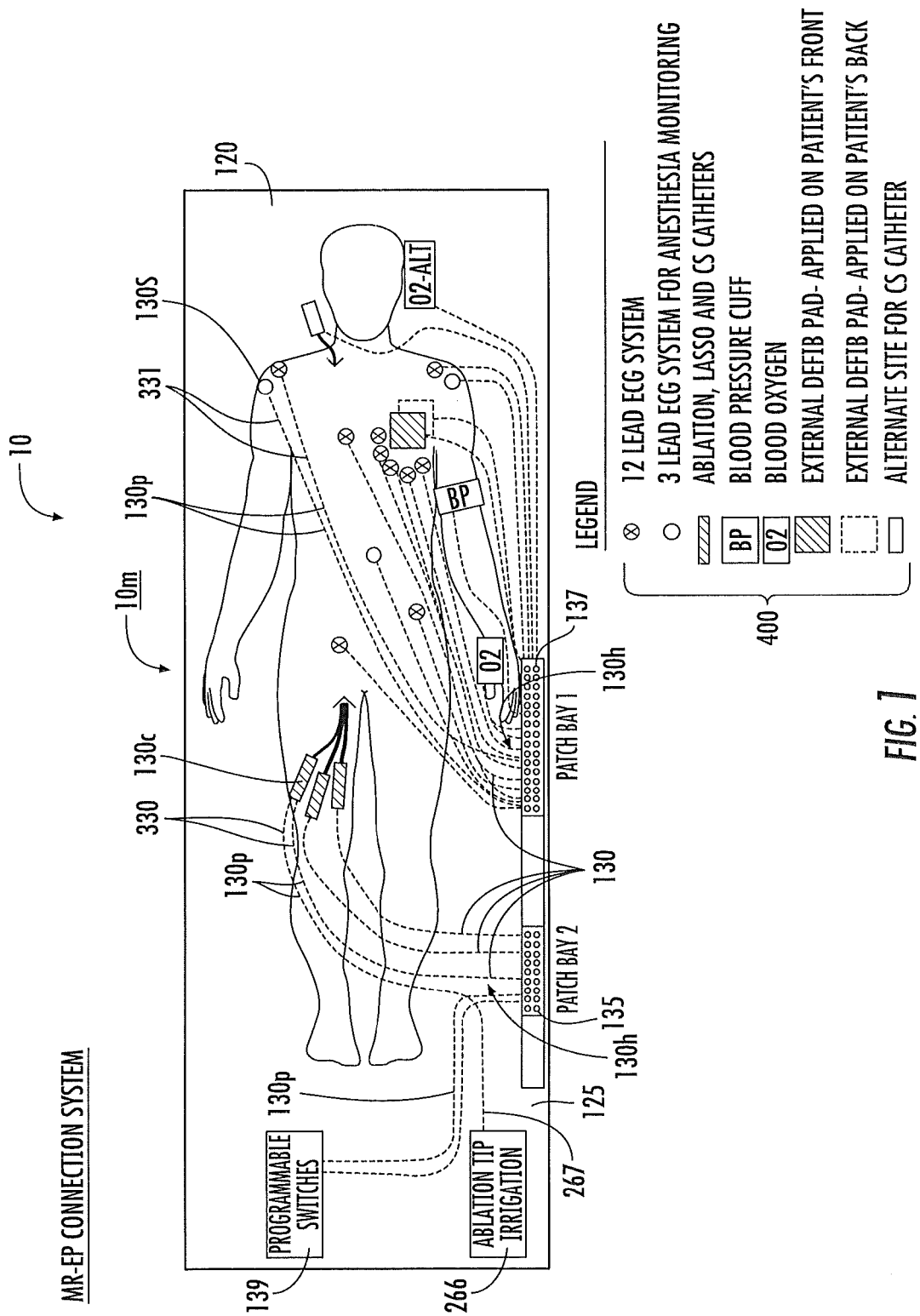
FIG. 1 is a top schematic view of a portion of an exemplary MRI interventional suite with a cable management system according to embodiments of the present invention.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "mat" refers to a pad or other device with electrical paths extending through portions thereof and that is typically resilient or flexible but has sufficient rigidity and/or thickness to hold the electrical paths and/or leads in a manner that does not cause discomfort to a user or patient. The electrical paths can be formed as internal wires, metallic traces or cables. For MRI procedures, the metal or conductor used to form the electrical paths in the mat (e.g., the leads held by the mat) can be non-ferromagnetic. The term "lead" means an electrical path created by one or more wires or conductors. The wires are typically insulated wires, particularly where exposed. The term "cable" is used interchangeably with the term "lead" and can also indicate a bundle or grouping of leads held together as a single cable group (e.g., cable bundle) for organization and reduced loose lengths of leads for routing. The cable bundle can be held together in a common sleeve and/or via tape for a desired length or lengths. The term "cable management system" refers to a structure such as a trough that holds and releases lengths of cable and can include a mechanism that cooperates with the cable/cable bundle to extend and retract a defined length of a lead or a cable (or a cable bundle) to adjust a length thereof in a room, typically a suspended length in a magnet room. The cable management system can be implemented from a ceiling or ceiling mounted trough or other support system. The term "trough" refers to a holding space and/or channel.

The term "MRI-compatible" means that a device is designed for use in an MRI environment and/or a device that can operate as intended in an MRI environment and/or not introduce artifacts into MRI signal data. As such, if residing within the high-field strength region of the magnetic field, the MRI-compatible device is typically made of a non-ferromagnetic MRI-compatible material(s) suitable to reside and/or operate in a high magnetic field environment. The current designations of MR-Safe and MR Conditional are defined in ASTM: F2503-05, American Society for Testing and Materials (ASTM) International, Designation: F2503-05. Standard Practice for Marking Medical Devices and Other Items for Safety in the Magnetic Resonance Environment. ASTM International, West Conshohocken, Pa., 2005. It is contemplated that where the components are used in an MRI Suite, the appropriate "MR Safe" or MR-Conditional icons will be used.

The term "high magnetic field" refers to magnetic fields above 0.5 T, typically between 1.5 T to 10 T, including about a 2.0 T and/or about a 3.0 T magnetic field. The term "remote" means that the so-called member, component or room is in another location, typically in a discrete or separate physical space, such as an adjacent room. Thus, the term "remote" includes on-site locations.

Generally stated, embodiments of the present invention solve a problem associated with undue lengths of cables that are typically used in some procedures and that can sometimes provide tripping hazards, randomly coil, kink or intertwine and/or that may provide MR incompatibility issues that inhibit safe and/or efficient surgical or diagnostic procedures. Embodiments of the invention provide cable management systems that have adjustable controllable suspended lengths of cable between a patch bay and a (ceiling mounted) cable management system that can allow a patient to remain connected to defined surgical monitoring and/or interventional components while being moved in and out of a magnet bore, such as at least about 3-6 feet, typically about 4-5 feet, in a longitudinal direction. In particular embodiments, the cable management system allows even greater movements (lateral, diagonal and/or longitudinal movements) out of the MR scan room, even out of the MR suite into an adjacent room. In this embodiment, the allowed translation distance can be at least about 15-20 feet while maintaining the electrical connections from the patient end to the system end cable connections.

Embodiments of the invention can shorten the distance between a patch bay and a distal end of a lead used during a procedure and/or may provide an organized orientation of a lead or leads from a patch bay to a patch panel and/or a remote device in a separate room, typically the control room (e.g., power source, RF source, workstation, monitor and the like).

Embodiments of the present invention may optionally, alternatively or additionally, configure a patch bay to incorporate circuit components for RF decoupling, tuning, filtering signal and the like, such as, for example, a PIN diode, a parallel resonance tank circuit tuned to an MR frequency and the like.

Figure 2:
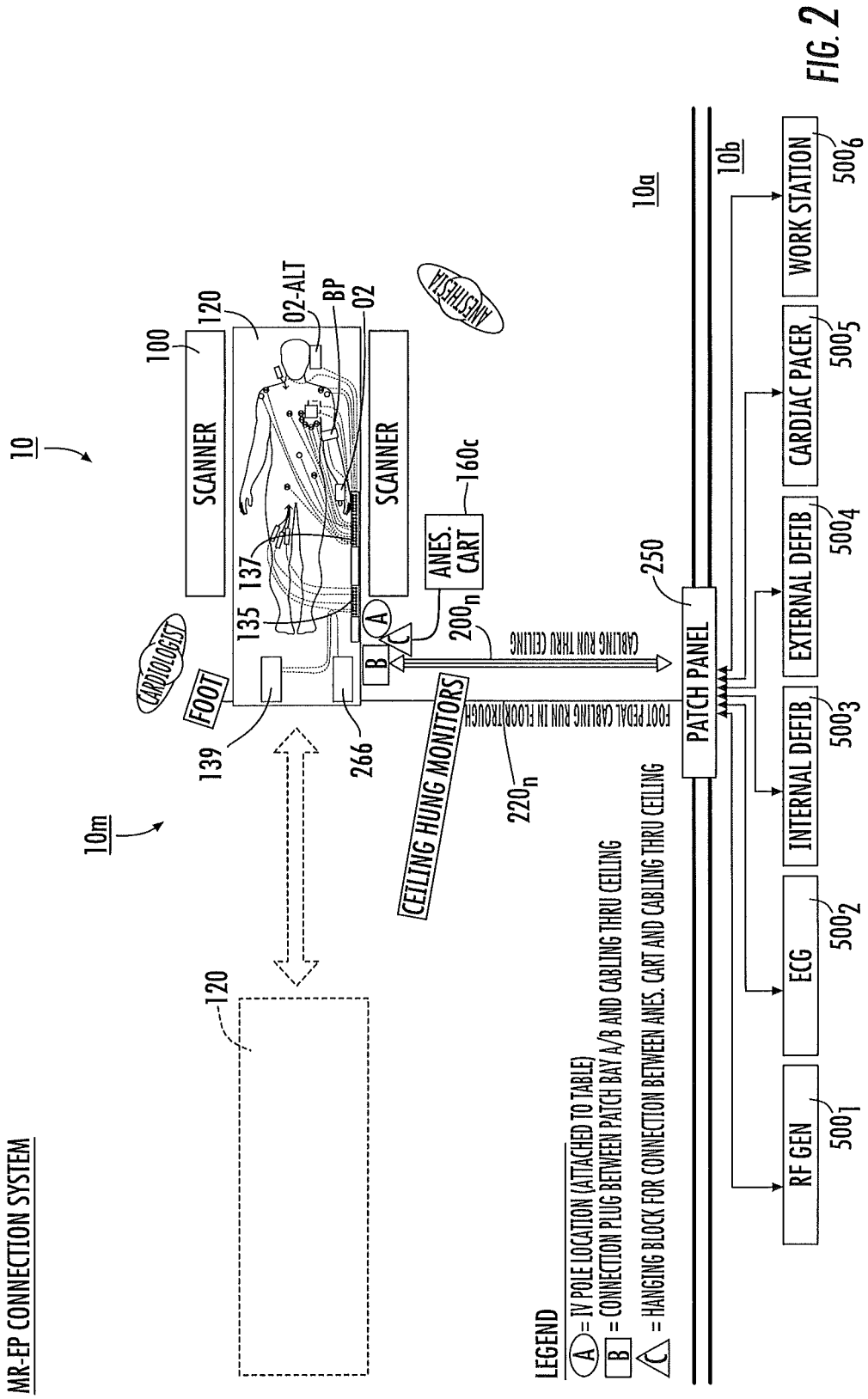
FIG. 2 is a top schematic view of an exemplary MRI interventional suite with a cable management system according to embodiments of the present invention.

Referring now to the figures, FIG. 1 illustrates a portion of an MRI Interventional suite 10 with scanner 100 (FIG. 2), a scanner table or bed 120, and an integrated cable management system 10*m* that manages lengths of cables or leads 130 that connect multiple patient components with external components. The cable management system 10*m* is configured to provide a desired length of cabling and can include a tensioner and/or other control mechanism that allows the suspended cable portion to have substantially the same tension (or "slack" amount when attached to the patch bay) irrespective of the length of the cable outside the ceiling. One end of the (patient side or "short") leads 130 connect to a patch bay 135, 137 residing proximate one edge portion of a scanner table 120 (or a mat 125 on the scanner bed (e.g., FIG. 7A). Some of the leads 130 (labeled in FIG. 1 as element 330) can connect to intrabody components such as intrabody catheters 130*c* while other leads (labeled in FIG. 1 as element 331) can connect to external components such as sensors 130*s*. Additional "long" interconnecting leads 200, 210 extend from the patch bays 135, 137 to remote components such as power sources, monitors, signal processors, computers, clinician workstations with displays, and/or controls (500*n*, FIG. 2). Although shown as connecting to connection blocks "B" and "C", one or more of the longer leads 200, 210, respectively, may directly connect to the "shorter" leads or patch bay 135, 137. Some or all of the remote components 500*n* (shown as components 500$_1$-500$_6$) can reside in a separate room (separated by an RF shield) of the MRI suite away from the patient and/or magnet 100. The cable management system 10*m* allows the patient leads 130 and the associated external leads 200n to remain in position and connected while allowing the patient to be translated longitudinally without requiring loose lengths of leads that may lie on a floor and/or that may interfere with the procedure. The system 10m can allow the patient to be translated in or out of a magnet bore (e.g., at least between about 4-5 feet) in the magnet room or optionally into an adjacent room (such as a conventional angio room associated with conventional EP MRI suites) as shown in FIG. 2 to allow a clinician direct access to a patient. The in-room cables 200n can connect to the respective remote components 500 via a patch panel 250 as is known to those of skill in the art.

It is noted that although particularly suitable for an MRI (cardiac) suite, the systems can be used with and/or configured (modified if appropriate or desired) for use with CT or other X-ray or alternate navigation systems and for other target regions/organs of the body.

Figure 3:
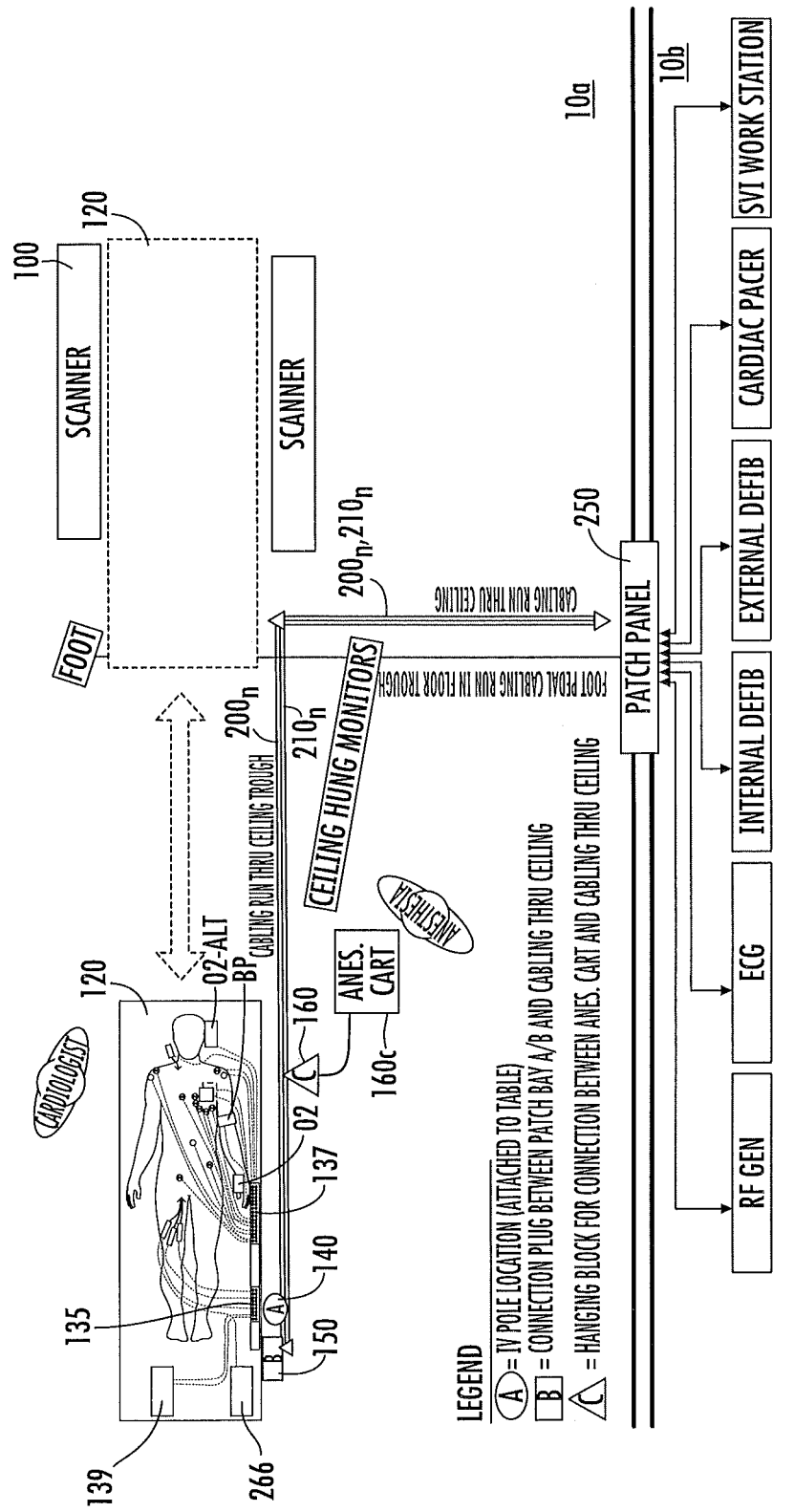
FIG. 3 is a top schematic view of the suite shown in FIG. 2 with the patient shown outside the MRI scanner with cables intact according to embodiments of the present invention.
Figure 4:
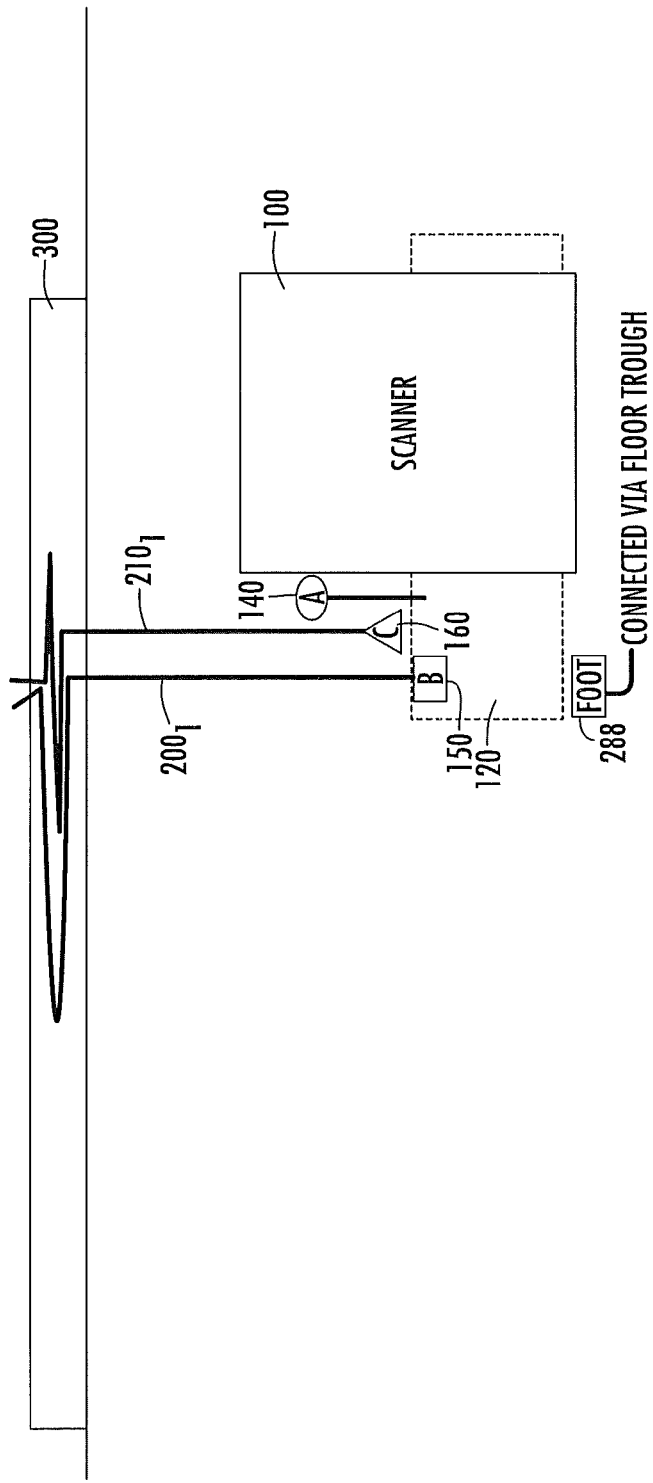
FIG. 4 is a side schematic view of a portion of the MRI suite with the cable management system shown in FIGS. 2 and 3 according to embodiments of the present invention.

FIG. 3 illustrates that the MRI suite 10 can include an IV pole 140 (typically attached to the scanner table 120). As shown, the system 10m can include a connection block 150 of cables 200n that are routed above the patient, typically through a ceiling (e.g., they extend up, through and above a ceiling 300) (FIG. 4). N "n" is typically between about 1-400 and more typically between about 5-100 connect to patch (connector) bay 135 and/or 137. Cabling 210n for anesthesia cart 140 can also be routed above the patient, typically through the ceiling 300 (where "n" is a number typically between about 1-400 and more typically between about 5-100). Alternatively, the cable management system 10m can reside below the ceiling, e.g., the cabling can be suspended from the ceiling or a support associated therewith rather than be held inside the ceiling.

Figure 5:
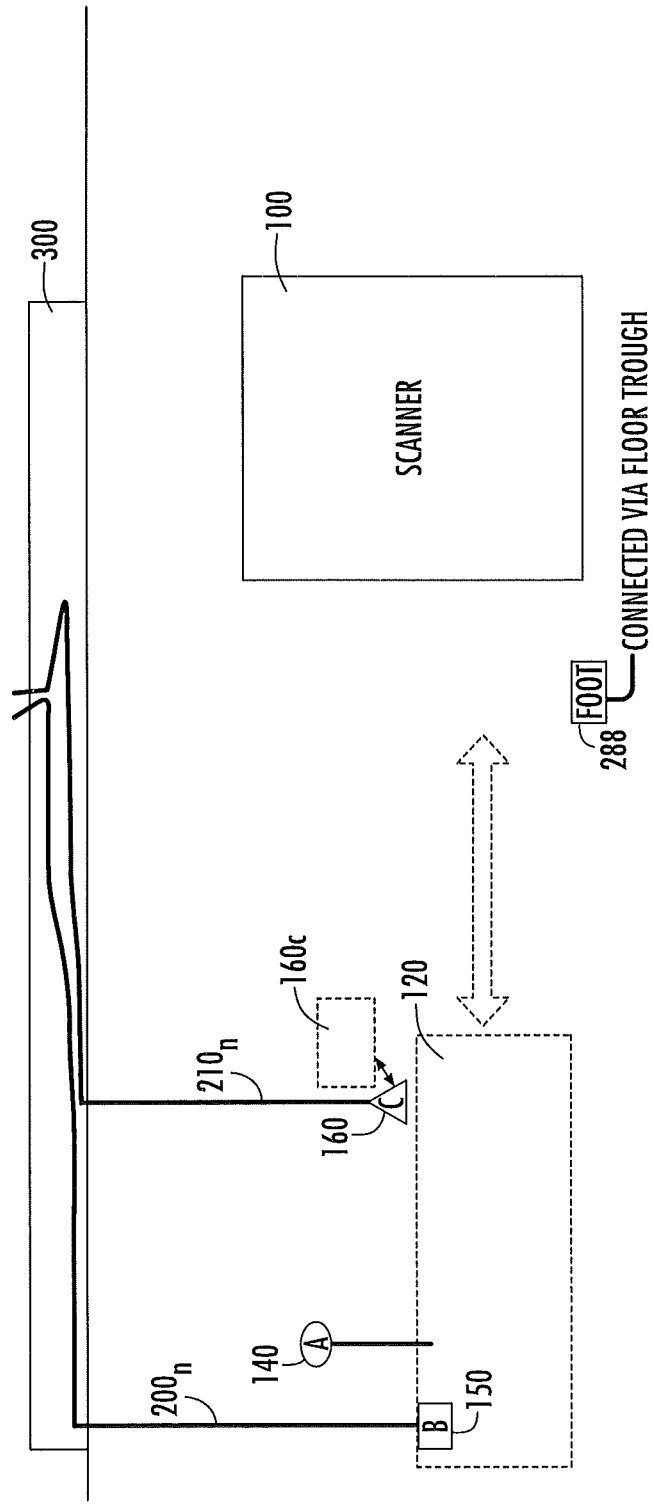
FIG. 5 is a side schematic view of the cable management system shown in FIG. 4 with the scanner table moved out of the MRI scanner and cables allowing for extension accordingly.

The cabling 210n to the anesthesia cart 160c can be separately adjustable in length apart from the bundles of cabling 200n that extends to one or both of the patch bays 135, 137 to allow for a clinician to place the cart 160c where desired irrespective of the location of the table 120. For example, in FIG. 4, the cart 160c and hanging block "C" are shown adjacent a foot end portion of the bed 120 outside of but next to the scanner 100. In FIGS. 3 and 5, lengths of the cabling 210n is extended and cart 160c and hanging block "C" are shown translated about 4-6 feet with the cart and block adjacent the head end of the bed 120 (while the connection plug B is adjacent the foot end of the bed). FIG. 5 shows the hanging block "C" adjacent the scanner magnet and cabling 210 retracted relative to FIGS. 3/5.

FIGS. 2 and 3 also illustrate that the MRI suite 10 can include a first room 10a with a patient and/or scanner 100 and a second room 10b with the remote components 500n. The cabling 200n, 210n extends through the ceiling 300 between the rooms 10a, 10b and can connect to the remote devices 500n (shown as $500_1$-$500_6$) through a patch panel 250. As shown, in some embodiments foot pedal cabling 220n can extend through a floor trough to the patch panel/second room 10b as well (where "n" is typically between about 1-100 cables).

Particular embodiments are directed to real time MRI-Guided EP (electrophysiology) interventional systems to treat atrial fibrillation that may require moving the patient table in and out of the scanner bore. During a procedure, it may be desirable to move a patient out of the scanner bore 100 to defibrillate the patient while leaving substantially all devices/leads in or on the place, which may not be able to be performed in the scanner bore.

As discussed above, the cable management system 10m can allow the patient to remain on the table while moving the patient in and out of the bore and also can allow all electrical and catheter connections to remain intact. The electrical and catheter connections and/or patch bay, can, in some embodiments, be configured to exit a foot end portion of the scanner bed (shown as about a long side toward the foot end of the scanner bore) or at other locations.

Embodiments of the invention configure leads (e.g., cables) used inside the scanner room 10a to be safe (heat-resistant) at frequencies associated with a plurality of different conventional and future magnetic field strengths of MRI systems, such as at least two of 0.7 T, 1.0 T, 1.5 T, 2 T, 3 T, 7 T, 9 T, and the like, allow for safe use in those environments (future and reverse standard MRI Scanner system compatibility).

Generally stated, cables, leads or other electrical paths 130 (330, 331), 200, 210 in the mat or table and/or outside the mat or table are exposed to high power RF pulse from the MRI scanner. These pulses can cause standing waves on the cables and leads. The cable management 10m can be configured so that some or all of the cables or leads are configured to prevent unwanted RF induced heating. This may be particularly true for any leads or cables inside a patient, contacting a patient, or adjacent the patient to prevent unwanted RF induced heating of the patient from induced current along the leads and/or to prevent interference in MR signal quality.

For example, as shown in FIG. 1, leads 330 forming a part of the electrical path 130p that connects intrabody devices and/or leads 331 forming a portion of the electrical paths 130p connecting external devices (e.g., ECG sensors) on the patient can be configured to have at least one conductor having a length with opposing distal and proximal end portions that turns back and forth along its length. The conductor may be configured to having at least one segment with a multi-layer coil configuration comprising a first forward coiled section that extends in a forward lengthwise direction for a first forward physical length, then turns to merge into a proximately positioned reverse coiled section that extends in a substantially opposing reverse lengthwise direction for a reverse physical length, then turns to merge into a proximately positioned second forward coiled section that extends in the forward lengthwise direction for a second forward physical length. See, e.g., U.S. patent application Ser. No. 12/047,832 for a discussion of different "back and forth" configurations (aka as the "Billabong"), the contents of which are hereby incorporated by reference as if recited in full herein.

Alternatively or additionally, one or more of the leads 130 (330, 331) and/or cabling 200, 201 may alternatively or additionally be configured to have high impedance. The term "high impedance" means an impedance that is sufficiently high to reduce, inhibit, block and/or eliminate flow of RF-induced current at a target frequency range(s) associated with the operational frequency of the scanner. The impedance has an associated resistance and reactance as is well known to those of skill in the art. Some embodiments of the leads can be configured to may provide an impedance of at least about 100 Ohms, typically between about 400 Ohms to about 600 Ohms, such as between about 450 Ohms to about 500 Ohms, while other embodiments provide an impedance of between about 500 Ohms to about 1000 Ohms or higher.

One or more of the leads 200, 210, 130 (330, 331) can include at least one coiled segment or circuit components that can be tuned. The term "tuned" with respect to a coil, means tuned to define a desired minimal impedance at a certain frequency band(s) such as those associated with one or more high-field MRI Scanner systems. When used with respect to a parallel resonant circuit with inductive and capacitive characteristics defined by certain components and configurations, the word "tuned" means that the circuit has a high impedance at one or more target frequencies or frequency bands, typically including one or more MRI operating frequencies. In general, discrete or distributed impedance elements such as inductors and/or capacitors or integrated capacitance, may be included in some or all of the leads 330, 331, 200, 210 for increasing impedance or tuning the local impedance maxima and providing desirable current suppression capabilities.

Figure 8:
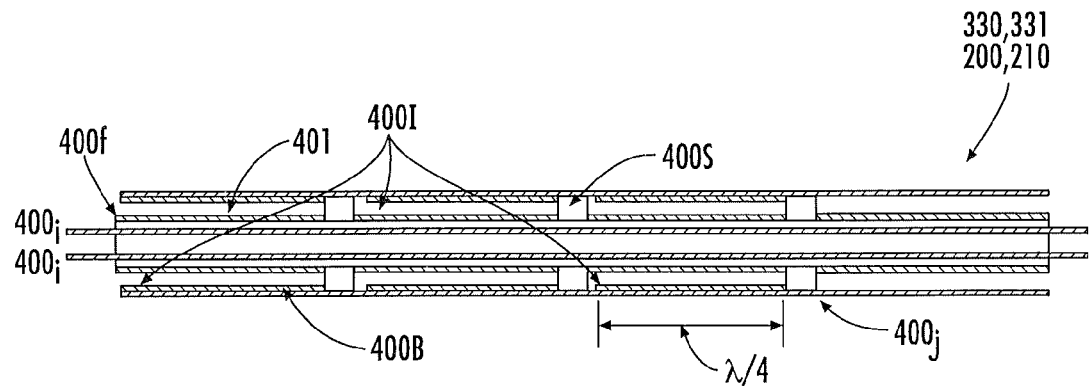
FIG. 8 is a partial section schematic view of an exemplary cable configured to inhibit RF induced standing waves.

FIG. 8 illustrates one particular (non-limiting) way to prevent the standing wave by creating tuned high impedance points 400I along the length of the cable 400 (e.g., 330, 331, 200, 210). This can be achieved by adding an additional braid 400B on top of the cable. The cable 400 can also include an inner foil shield 400f, at least one (shown as two) inner signal lines 400i, outer PVC jacket 401, outer heat shrink jacket 400j, and solder joints connections 400s to inner shield 400f. The cable creates open circuits and short circuits along the length as shown in FIG. 8. By setting the length of such sections to quarter lambda length of the RF frequency, periodic high impedance points 400I are created along the cable length. However, as discussed above, other methods for suppression of induced RF currents can additionally or alternatively include cable traps, the so-called 'Billabong' leads (with the series of forward and reverse segments), RF chokes and carbon wires in leads.

In some embodiments, some of all of the leads or electrical paths 130, 330, 331 (and/or 200, 210) can be configured with one or combinations of, RF chokes, RF traps, Balun circuits, high impedance, carbon wires in leads and/or a series of reverse and forwards sections. See, e.g., U.S. Patent Application Publication No. US-2008-0243218-A; U.S. patent application Ser. Nos. 112/090,583 and 12/090,583; and U.S. Pat. No. 7,561,906, the contents of all of which are hereby incorporated by reference as if recited in full herein.

The cable management system 10m can provide connections from the patient end (table 120, mat 125, or patch bay 135, 137) to the patch panel 250 that are simple, clean and easy to connect/disconnect and have adjustable length.

In some embodiments, the system 10 is configured to allow an Anesthesiologist to move the anesthesia/Patient monitoring cart 160c to be nearer to a patient's head during the procedure while allowing automatic take-up or extension of cabling. The connections from the patient to the anesthesia cart are simple, clean and easy. The system 10 can accommodate independent movement of anesthesia cart 160c and associated cable block connection 160 (FIG. 5) and independent length adjustment of cables 200n, 210n.

FIG. 2 illustrates the patch bays 135, 137 attaches to cabling 200n hanging down from ceiling via connection (plug or receptacle) block (B) 150. The anesthesia cart 160c attaches to separate cabling 210n that hangs down from ceiling via hanging connection (plug or receptacle) block (C). As also shown in FIG. 2, the electrical leads and fluid catheters exit the scanner bore from a foot end portion to facilitate patient movement. The designation "block" with respect to connections "B" and "C" is used in a broad sense to mean releasable connector configurations and is not intended to limit the configuration of the actual connection.

The system 10 and cable management 10m can put all key EP equipment outside of the scanner room 100 (10a) so that conventional equipment can be used for this procedure in an adjacent room 10b. This design will provide electrode signal paths and equipment control signal paths in and out through the patch panel 250. The control of EP equipment may be performed by a technician in the control room or by remote control by physician via programmable switch box.

FIG. 3 illustrates the scanner table/bed 120 (with patient) after the patient has been moved out of the scanner 100 with the cabling adjusted (extended) from the cable management system 10m to provide additional lengths to keep the connections intact without undue lengths of cable while allowing the desired longitudinal movement with the patient remaining on the table 120. This can allow a clinician access to the patient in the scanner room 10a while connections are maintained (such as for defibrillation if necessary). Cabling from ceiling connected to plug/patch bay (B) moves through ceiling (or below the ceiling) as the table 120 is moved. Cabling from or below the ceiling that is connected to the hanging Block (C) for the anesthesia cart can move separately through the same trough in the ceiling or through a separate trough as desired. The IV pole (A) can move with the table 120.

FIG. 4 illustrates lengths of cable looping in a ceiling trough for connection (B) and (C) while the patient is in the scanner 100. The trough may be placed above the ceiling such that it is not readily visible to a user or may be suspended from the ceiling and exposed for viewing or placed in an enclosed housing in or suspended from the ceiling for sterility or cleanliness. The trough may also or alternatively be supported by the walls or other frame support components. In operation, cabling 200n, from the cable management system 10m (typically from ceiling 300) connected to connection "B" 150 can slidably move through a trough as the table is moved into position, typically to allow between at least about 3-6 feet of take-up and extension into and from the room. In lieu of or additionally with the cable looping as shown in FIG. 4, the system 10m can be configured to provide the adjustable lengths in storage above or below the ceiling using a take-up reel or other take-up and extension mechanisms to facilitate automatic cable management. Cabling 210n from the ceiling 300 (or ceiling mounted cable support) connected to hanging block (C) 160 for Anesthesia Cart 160c can move separately through the same or a different trough. In this embodiment, hanging block (C) 160 is not typically connected to the table 120 to allow for varying linear positions during scanning/ablation procedures and/or defibrillation.

FIG. 5 is similar to FIG. 4 but illustrates that the system 10 allows the patient table 120 to be moved out of the scanner 100 and into position for defibrillation or other patient access with the cabling remaining attached to the patient components and intact and without excess cabling extending between the patch bay and the cable management system 10m. Cabling 200n connected to patch bay (B) 150 is now in an extended position. As shown, cabling 210n from ceiling 300 connected to hanging block (C) 160 for Anesthesia Cart 160c is also extended, but will typically not need to travel as far as the cabling for (B). As is also shown, the IV Pole (A) 140 is attached to table and the foot pedal 288 (associated with ablative energy control for ablation) does not need to move and can be connected via a floor trough (or in an existing ceiling trough(s) or another ceiling trough).

Figure 6:
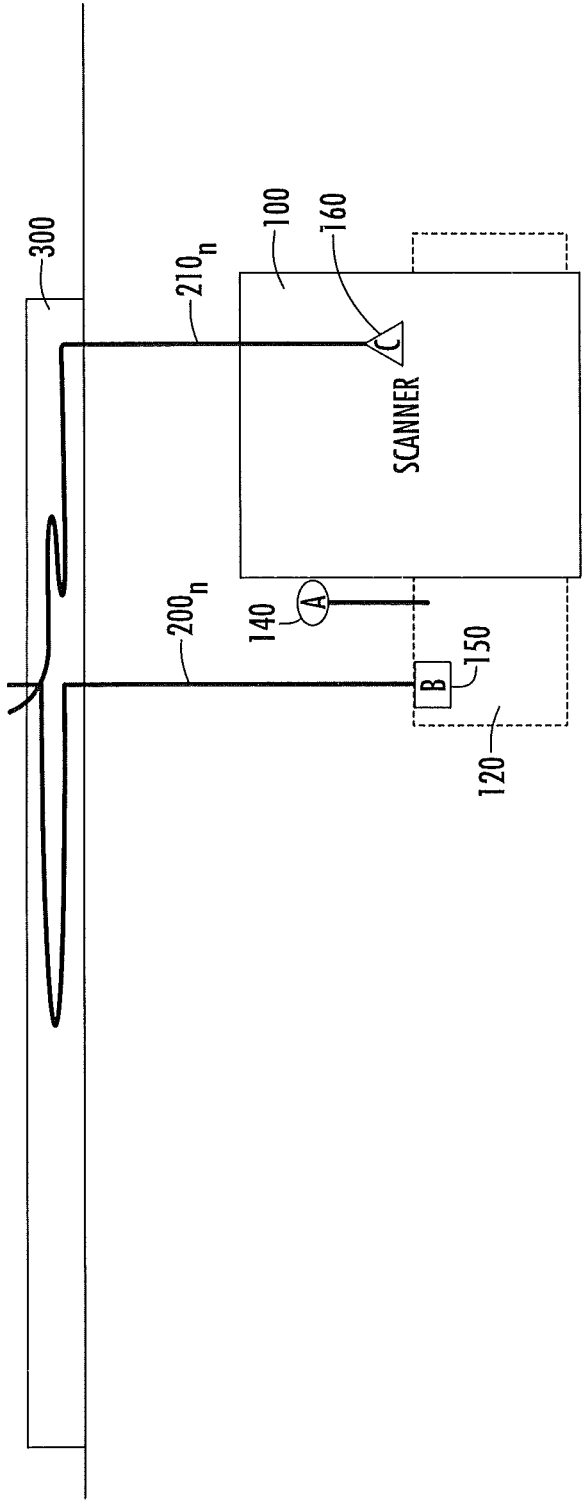
FIG. 6 is a side schematic view of the cable management system shown in FIGS. 4 and 5 with the anesthesia cart moved closer to a patient's head and with the cables from two different connections (patch bay "A" and/or "B") and cart (c) having separately adjustable lengths according to embodiments of the present invention.

FIG. 6 shows at least one cable bundle looping in ceiling trough for connection plug (B) (that connects to patch bays 135, 137) and another cable bundle for hanging block (C). The patient is in the Scanner 100 and the Anesthesia Cart 160c and cabling block 160 can be moved closer to the head of a patient. Cabling 210n from ceiling 300 connected to connector patch bay plug (B) 150 is now substantially in the original position and the patient is in position for a scanning/interventional procedure. As discussed above, cabling 210n from ceiling 300 connected to hanging block (C) 160 for Anesthesia Cart 160 moves separately through a trough in the ceiling 300, if desired. As shown, the Anesthesia Cart 160c and hanging block 160 have been moved toward the patient's head.

Although shown as a ceiling mounted cable management system 10m, other embodiments of the invention alternately or additionally employ floor routed cabling with length adjustment (retract and extend) to allow for take-up of excess length to provide the desired extension length. The cable management systems 10m can be configured so that the cables have substantially the same slack (same amount of looseness or tension) whether the scanner table 120 is inside or outside the MRI scanner 100. The length adjustment in the scanner room 10a can be at least about 3-6 feet while maintaining the electrical connections of at least some, if not most or all of the ECG sensors 130s (FIG. 1) and at least one intrabody catheter 130c (FIG. 1). In other embodiments, the length adjustment allows at least one bundle of the cables 210n, 200n to extend between about 15-20 feet (and out of the MR suite) as discussed above, while maintaining the electrical connections of at least some, if not most or all of the ECG sensors and at least one intrabody catheter.

Figure 7A:
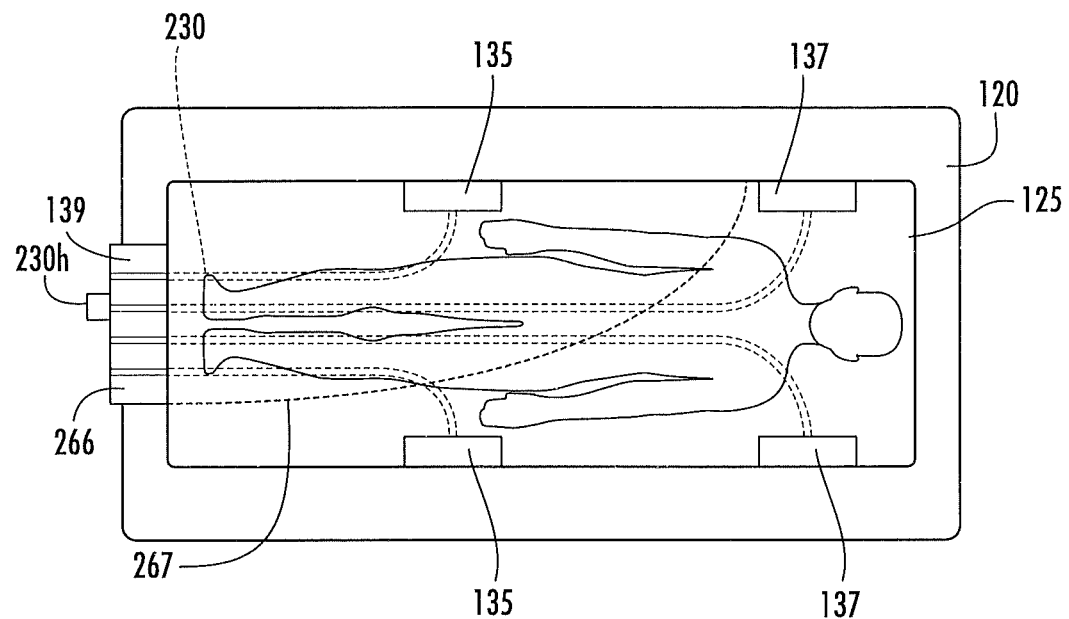
FIG. 7A is a schematic illustration of a mat with integral electrical and/or fluid paths according to embodiments of the present invention.
Figure 7B:
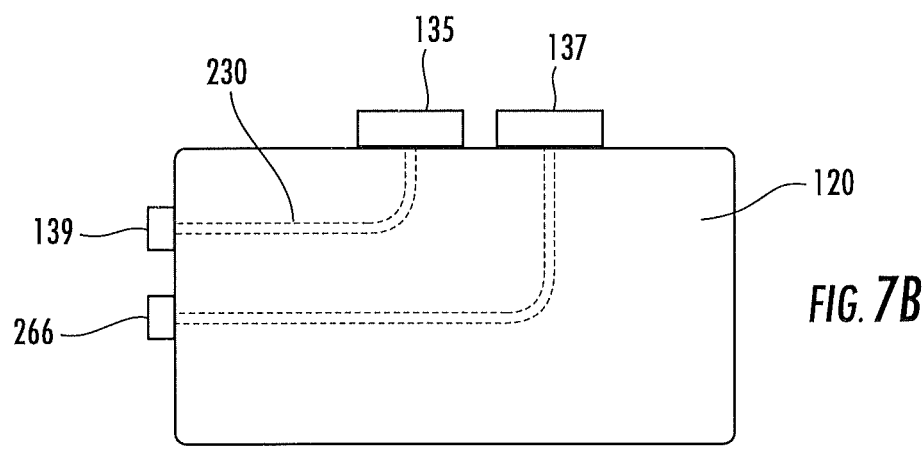
FIG. 7B is a schematic illustration of a patient support table with integral electrical and/or fluid paths according to embodiments of the present invention.

As shown in FIG. 7A, the system 10 may optionally include a medical mat 125 that resides on the table 120. The mat 125 can be configured with integral electrical paths 230 and one or more hubs and/or patch bays A/B, 135, 137. In other embodiments, the table 120 can be configured with integral electrical paths 230 and one or more hubs and/or patch bays A/B, 135, 137. FIG. 7B illustrates that the table 120 can alternatively or additionally include integral electrical paths 230 or a fluid path.

In some embodiments, the mat 125 or table 120 can define at least a portion the electrical paths from the patch bays 135 and/or 137, the mat 125 or table 120 can be configured to provide a desired number of discrete electrical paths 230, typically between about 5-1000, and more typically between about 10-500, such as between about 12-200, and, in some particular embodiments between about 60-120, but lesser or greater numbers of paths can be used. As shown, for example, in FIG. 7A, in some embodiments, at least one electrical path 230 extends from a foot end portion to exit or end at a target location over, under or into a patient. The electrical paths 230 may all converge into one or more electrical input "hubs" 230h associated with patch bays 135, 137. The term "hub" means that all or substantially all of the electrical paths start from one or more connectors/inputs at this location. The hub location(s) may also provide the programmable switches and/or irrigation 139 or, where used, these components may be integrated into the mat 125 and/or table 120 at discrete (end) locations as shown in FIG. 7B.

The systems can be used to control the orientation and/or reduce the lengths of loose cables associated with conventional procedures for ease in access to the patient or tools, to improve patient transportability, to provide a more efficient medical set-up, and/or to arrange the cables so that they do not loop or cross-over each other to inhibit heating or burns that may be induced due to the RF environment in MRI-guided procedures.

The mat, where used, can be sterile (meaning that it meets clinical cleanliness standards for medical procedures) and may optionally be single-use disposable. Alternatively, or additionally, a sterile cover or case can be used as appropriate. The mat may directly or indirectly contact the patient. The mat may cover all or substantially all of the patient support surface or may be smaller to occupy only a sub-portion of the support surface. For additional description of exemplary medical mat configurations, see, co-pending U.S. patent application Ser. No. 12/627,587, the contents of which are hereby incorporated by reference as if recited in full herein.

The patch bays 135, 137 (e.g., "1 and 2" and/or "A and B") can include standard connectors such as BNC connectors, coaxial connectors and the like or the connectors may be customized connectors. For some particular embodiments, such as for use in cardiac EP procedures, the outlet connectors typically include Hypertronoics™ multi-pin connectors for an ablation catheter, ECG leads, coronary sinus catheter, lasso catheter, defibrillation and pacing devices.

The patch bays 135, 137 may include color-coded connectors to correspond with external leads 200n, 210n, as appropriate to facilitate set-up and proper connection. The connectors may have different shapes to inhibit improper connection of external leads. Although shown in an exemplary embodiment as two separate patch bays along a common (long) side of the patient table, the patch bays 135, 137 can be configured as a single bay or more than two bays and can be spaced apart and/or placed at different sides of the table.

As shown in FIGS. 9-12, at least one of the patch bays 135, 137 can include one or more filters 135f, 137f for one or more lead 130, 200 via one or more connector provided by the patch bay(s). One or more of these filters may also or alternatively optionally be integrated in the mat 125, table 120 or lead 130 (330, 331), 200, 210.

Figure 9:
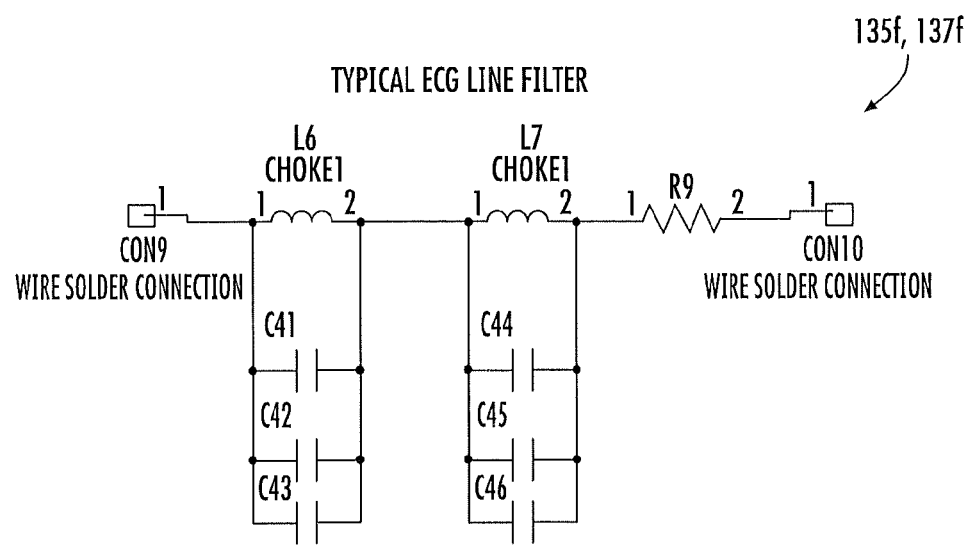
FIGS. 9-12 are circuit diagrams of examples of filters and/or circuits that can be incorporated into one or combinations of a patch bay, mat, table and/or lead according to embodiments of the present invention.

As shown in FIG. 9, an exemplary filter configuration is shown. CON9 (connector 9) is connection to sensing electrode on catheter 130c (FIG. 1) while CON10 (connector 10) is connection to the ECG recording system. L6, C41, C42 and C43 form a resonant circuit that blocks out RF signals from the MRI scanner, e.g., 123 MHz on a 3 T system. L7, C44, C45 and C46 form a resonant circuit that blocks out RF signals from the ablation signal generator, e.g., 500 KHz. R9 is a resistor (typical value about 5 Kohm) that further isolates detection circuits from other sources of signals like the MRI scanner and the ablation signal generator.

Figure 10:
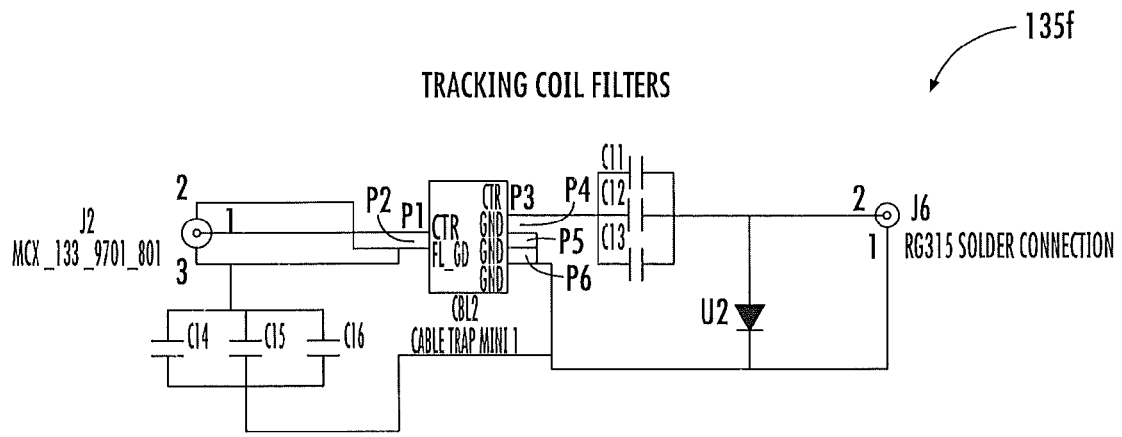

In some embodiments, one or more (if more than one is used) of the intrabody catheters 130c (FIG. 1) can include tracking coils as is well known to those of skill in the art. The tracking coils may be used for visualization of catheters and other devices inside the body. MRI scanner generates high power RF that may cause standing waves to form on the conductive surfaces like wires and cables inside the catheters. This can result in local heating/burns on the patient's body. FIG. 10, illustrates tracking coil filters 135f that may be integrated into the patch bay 135. CBL2 is a cable trap that is located inside the patch bay 135. However it may be totally or partially included in mat 125 or table 120. The cable trap prevents RF standing waves from being conducted to the scanner ground. It is tuned to frequency (e.g., 123 MHz) by capacitors C14, C15 and C16. Tracking coils may be decoupled externally by PIN diode U2 which is shorted by DC bias from the MRI scanner controller. C11, C12 and C13 provide a DC block that prevents PIN diode bias from going into the tracking coil but allow RF signals from the tracking coil to pass un-attenuated to radio receiver in the MR scanner via connector J6.

Figure 11:
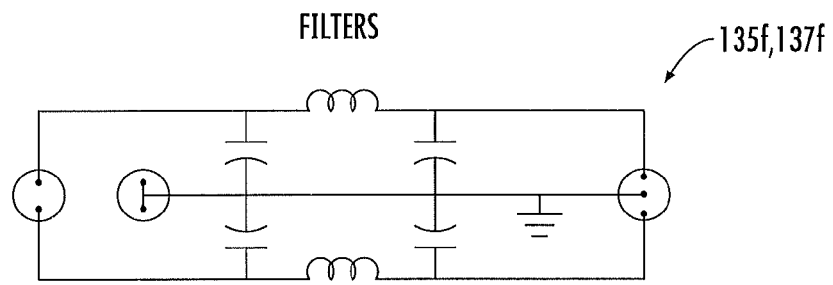
Figure 12:
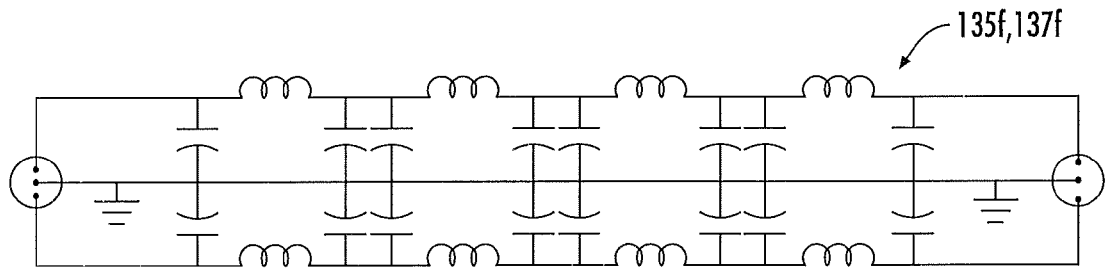

FIGS. 11 and 12 illustrate other filters 135f, 137f that can be used for isolating electrical systems from the MRI scanner. FIG. 11 illustrates a dual line low pass PI filter. FIG. 12 illustrates a dual line lattice filter. The filters 135f, 137f can be integrated into the patch bay(s) 135, 137. Alternatively, all or portions of the filters can be integrated into the corresponding lead 130, 200.

Figure 13:
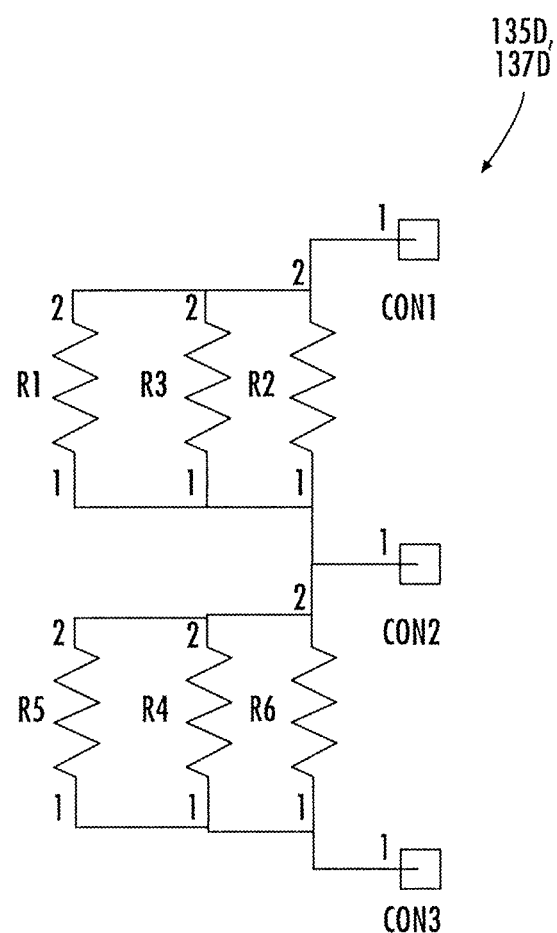
FIG. 13 is a circuit diagram of a device detection circuit that can be incorporated into a mat, table and/or patch bay according to embodiments of the present invention.

As shown in FIG. 13 at least one of the patch bays 135, 137 can include a device detection circuit 135D, 137D. A monitoring circuit can automatically detect which devices are connected to the patient patch bay 135, 137 and/or mat 125. One way this can be achieved is by using ID resistors in the patch bay and/or mat as well as in various devices that connect thereto. The MRI scanner computer or processor or the clinician workstation module or processor can monitor resistors via connections CON1, CON2 and CON3. Devices like the ablation catheter 130c (FIG. 1) can have built-in resistors that modify the resistance by lines that connect to CON1, CON2 and CON3. Variation in resistance values helps the monitor which device is connected. Once that determination is made the scanner may automatically load special acquisition parameters, display parameters and update the progress of the procedure to display on the workstation $500_6$ (FIG. 2), for example.

FIGS. 2-3 illustrate six different subsystem remote components 500 with surgical tools 400 (FIG. 1) connected to a patient for an MRI-guided cardiac EP procedure. As shown, the system includes a lasso catheter, a cardiac sinus catheter (via the leg or neck), an ablation catheter (such as a multi-electrode ablation catheter or cryogenic-based catheter), multiple lead (e.g., 12-lead) ECG sensors (shown with 10), 3 lead ECG sensors for anesthesia monitoring, a lead to a blood pressure cuff, a lead for a blood oxygen sensor, leads for external defibrillation pads (front and back). The sub-systems include a clinician workstation with display/monitor for at least one display of EP mapping and at least one display for the ECG Monitor (which may include ceiling hung). In operation, ablation energy is applied to target cardiac tissue using the ablation catheter, the ECG signal can be monitored using the internal ECG signals and/or using external leads of the ECG sensors and the EP of the heart is mapped (and displayed) (generating an electroanatomical map) using the lasso and/or sinus catheters. Other patient monitoring leads/systems can be used including respiratory and blood pressure, for example.

EP clinical procedures involve recording and displaying in real-time numerous external and internal ECG signals. A coronary sinus catheter simultaneously measures as many as fourteen different ECG signals from inside the patient's heart (and may measure less or more than fourteen). In such an embodiment, these signals come down fourteen different wires down the catheter and the output connector has at least fourteen pins to transfer these measurements to the sub-systems that process these measurements. Similarly, the output connector of the lasso catheter has eight ECG signal pins while the ablation catheter has between about two to four ECG signal pins and two tip temperature pins. The external ECG can be recorded separately, typically using twelve (12) patch electrodes. Besides recording ECG, some of the same connector pins are used for externally pacing and/or defibrillating the patient's heart. In the ECG monitor subsystem fractionated ECG signals are displayed on a monitor and these signals guide the physician to specific target sites. A physician typically refers back to this monitor to confirm success of ablation procedure. Further, these ECG signals are one of the inputs used to generate the electro-anatomical map by the workstation subsystem.

Where used, the mat 125 (FIG. 7A) can be formed of one or more materials. The outer surfaces can be formed of a material(s) that is substantially impermeable to fluids. According to some embodiments, the mat can include a biocompatible polymeric material, such as those suitable for use in MRI systems. Exemplary polymeric materials may include polyvinyl, PET, silicone, polyethylene, polyurethane, and/or polyamide. Where the mat contacts the patient, the mat may be configured to provide heating or cooling as desired for patient comfort or treatment. Where the patient lies on the mat, the mat may be configured to provide cushioning using an air pocket, flexible soft material such as memory foam and/or gel material for patient comfort. Where the mat lies on the patient, the mat can be configured to be light weight and substantially conformable to the patient.

The system 10 can include one or more fluid passages/tubes 267 incorporated into the scanner table 120 and/or mat 125 that can be used to collect or supply fluid from ablation tip irrigation source 266 and/or to connect to a fluid source to allow medicines and/or drugs to be delivered to a patient, such as via IV drips, or that circulates fluid for heating and/or cooling.

One or more of the electrical paths 130 can include circuits such as filters that can facilitate signal acquisition or transmission (e.g., reduce noise, improve SNR and the like). As shown, for example in FIG. 1, one or more of the electrical paths 130p can include a programmable switch 139.

The MRI suite 10 and/or cable management system 10m can be used for other MRI (and non-MRI) procedures including brain surgery and other cardiac surgeries, and diagnostic and interventional procedures for other anatomical locations of the body.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A system for an MRI diagnostic or interventional procedure, comprising:
    a patient support table configured to move a longitudinal distance in and out of a bore of a magnet associated with an MRI scanner in an MR scanner room of an MR suite;
    at least one patch bay of connectors extending along at least one side and/or foot end portion of the table;
    a plurality of first leads, at least one that extends from at least one of the patch bay connectors to connect at least one intrabody device;
    a plurality of second leads having opposing first and second ends, the first ends of the second leads connect directly or indirectly to the at least one patch bay in communication with a respective one or more of the first leads via the at least one patch bay, wherein the plurality of second leads are held in at least a first cable bundle and the first cable bundle extends away from the patch bay with the second ends of the second leads configured to attach to remote devices held in a separate room away from the MR Scanner room of the MR suite, separated by an RF shield; and
    a cable management system in communication with the first cable bundle, wherein the cable management system is configured to extend and retract the first cable bundle to automatically adjust a length of the first cable bundle in the MR scanner room whereby the second leads remain above a floor in the MR scanner room while connected to the at least one patch bay and the remote devices as the patient support table is moved in and out of the bore of the magnet associated with the MRI scanner.

2. The system of claim 1, wherein the at least one patch bay resides on an outer perimeter of a mat having integrated electrical paths residing on the patient support table.

3. The system of claim 1, wherein the patient support table also includes a programmable switch spaced apart from the at least one patch bay of connectors, the programmable switch residing on one short end portion of the patient support table forming part of an electric path for one or more of the at least one intrabody device.

4. The system of claim 1, wherein the at least one patch bay comprises at least one electronic decoupler circuit and/or RF filter therein.

5. The system of claim 1, wherein the at least one patch bay comprises a device detection circuit in communication with a remote monitor via at least one of the second leads in the first cable bundle.

6. The system of claim 1, further comprising a second bundle of leads with a length and opposing first and second ends in communication with the cable management system to provide length adjustment in the MR scanner room whereby the second bundle of leads is held suspended above the patient with the first end merging into a movable hanging block that is in direct or indirect communication with an anesthesia cart and the second end is in communication with a remote monitor held in the separate room as one of the remote devices, and wherein the length of the second bundle of leads in the MR scanner room can be separately adjusted from the cable bundle extending to the at least one patch bay.

7. The system of claim 1, further comprising at least one programmable switch in the at least one patch bay in communication with at least one of the connectors.

8. The system of claim 1, wherein the cable management system is provided in the MRI suite as an integrated cable management system that is supported by a ceiling or resides in the ceiling, and wherein the cable management system comprises a trough which allows the at least one cable bundle to automatically slidably extend therefrom and retract therein in response to movement of the patient support table to allow a patient to be moved longitudinally on a patient table in and out of the magnet bore while the first leads remain attached to components in contact with the patient and the at least one patch bay and the second leads are suspended above the patient and remain directly or indirectly attached to the at least one patch bay and the remote devices through the RF shield, and wherein the first cable bundle has substantially the same slack whether the patient support table is located inside or outside the bore of the MR scanner by way of the longitudinal movement.

9. The system of claim 1, wherein the system is configured as an MRI cardiac system, and wherein the first leads are in communication with defined cardiac devices including at least one ECG sensor and/or one or more of a loop or lasso catheter, coronary sinus catheter or ablation catheter and an opposing end of the first leads are connected to the at least one patch bay, wherein the cable management system provides adjustable lengths of the second leads that allow a patient to be moved longitudinally in and out of the magnet bore while the patient remains on the table and while electrical connections between the first and second leads, the defined cardiac devices and cooperating remote devices in an adjacent control room as the separate room are maintained.

10. The system of claim 1, further comprising a connection plug residing at the first end of the first cable bundle, wherein the second leads connect to the at least one patch bay through the connection plug.

11. The system of claim 1, wherein the longitudinal movement is at least about 4 feet, and wherein the cable management system is configured to control slack so that at least one cable bundle has substantially the same slack whether the patient support table is located inside or outside the magnet of the MR scanner by way of the longitudinal movement.

12. An MRI cardiac electrophysiology ("EP") interventional system, comprising:
(A) a magnet room comprising:
an MR magnet with a magnet bore and patient support table;
at least one patch bay of connectors on the patient support table;
a plurality of (electrocardiogram) ECG sensors positioned on and/or in a patient, the ECG sensors having respective first leads attached to the at least one patch bay;
at least one intrabody catheter being in electrical communication with the at least one patch bay;
a cable management system holding a length of at least one cable bundle above a patient, the at least one cable bundle comprising a first cable bundle with a plurality of long leads having opposing first and second ends, the long leads configured to directly or indirectly connect to the at least one patch bay; and
(B) a control room located adjacent the MR magnet room and separated by an RF shield in communication with the leads held by the at least one cable bundle, the control room comprising:
at least one cardiac surgical device including an ECG monitor, an RF generator, an internal defibrillator, an external defibrillator, a cardiac pacer, and a workstation with a display, wherein the at least one cardiac surgical device is in communication with at least one respective lead from the at least one cable bundle to electrically connect the at least one intrabody catheter and/or ECG sensors,
wherein the cable management system is configured to extend and retract the at least one cable bundle to allow a least the first cable bundle to have an adjustable suspended length in the magnet room while (a) the at least one cable bundle is suspended above a floor of the magnet room and (b) the first ends of the long leads in the first cable bundle remain connected directly or indirectly to the at least one patch bay and the second ends remain connected directly or indirectly to the at least one cardiac surgical device in the control room as (a) the patient support table is moved in and out of the bore of the magnet inside the magnet room; and optionally (b) the patient support table is moved out of the magnet room to an adjacent room.

13. The system of claim 12, wherein the adjustable length is between about 4-20 feet, and wherein the cable management system is configured to control slack so that at least the first cable bundle has substantially the same slack whether the patient support table is located inside or outside the magnet bore of by way of the longitudinal movement.

14. The system of claim 12, wherein the at least one patch bay comprises at least one RF decoupling and/or filter circuit.

15. The system of claim 12, wherein the cable management system is provided in the magnet room as an integrated cable management system with a trough that is supported by the ceiling or resides in the ceiling, and wherein the cable management system slidably extends and retracts lengths of the at least one cable bundle automatically in response to movement of the patient support table to allow a patient to be moved longitudinally on the patient table in and out of the magnet bore of the magnet room while the first leads remain attached to components in contact with the patient and the at least one patch bay and the long leads remain directly or indirectly attached to the at least one patch bay and the at least one cardiac surgical device in the control room.

16. The system of claim 12, wherein the at least one cable bundle further comprises a second bundle of leads with opposing first and second ends in communication with the cable management system to provide length adjustment in the magnet room whereby the second cable bundle is held suspended with the first end connected to a moveable hanging block in communication with an anesthesia cart and the second end in communication with a remote monitor, and wherein a length of the second bundle of leads in the magnet room can be separately adjusted from the first bundle extending to the at least one patch bay.

17. The system of claim 12, wherein the at least one patch bay is provided by a mat residing on the patient support table.

18. The system of claim 12, further comprising a connector plug residing proximate the patient table and directly connected to the second end of the leads of the first cable bundle, wherein the connector plug directly connects to the patch bay to electrically connect the long leads to the first leads.

19. An MRI scanner room with a magnet and an integrated cable management system, comprising:
a patient support table configured to move a longitudinal distance in and out of a bore of the magnet associated with the MR scanner room of an MR suite, wherein the patient support table has or holds at least one patch bay; and
a cable management system held in or by a ceiling of the MR scanner room configured with a trough and an extension and retraction mechanism to automatically take-up of an excess length of at least a first suspended cable bundle into the trough and extend an additional length of the first suspended cable bundle from the trough in response to movement of the patient support table in and out of the bore while (i) maintaining a desired slack in and/or length of the first suspended cable bundle when leads of the first suspended bundle are connected to devices in a control room of the MR suite through an RF shield and (ii) keeping an end of the suspended first cable bundle above a floor of the scanner room substantially at a height associated with a top portion of the patient support table in the scanner room, wherein the patch bay is adapted to connect one or more leads from the first suspended bundle to one or more leads connected to at least one intrabody device to thereby connect a remote device to the at least one intrabody device.

20. A method of performing CT or MR guided cardiac electrophysiology ("EP"), comprising:
providing a table with at least one patch bay of connectors;
inserting at least one intrabody interventional device into a patient;
positioning ECG sensors on and/or in the patient;
connecting leads attached to the at least one intrabody device and sensors to the at least one patch bay;
attaching at least a first cable bundle with cables to the at least one patch bay to electrically connect the intrabody catheters and the sensors to remote monitoring and/or control components; and
extending and retracting lengths of the first cable bundle of cables from inside a ceiling or from a ceiling-mounted cable management system in response to moving the patient on the table longitudinally while maintaining the electrical connections between the intrabody catheters and sensors and the remote components, wherein the cable management system is configured to control slack so that the first cable bundle has substantially the same slack whether the patient support table is located inside or outside an MR or CT scanner by way of the longitudinal movement.

21. The system of claim 20, wherein the at least one patch bay is arranged as at least first and second hubs that incorporate a plurality of adjacent connectors, and wherein at least one of one of the adjacent connectors has circuit components for one or more of RF decoupling, tuning and filtering signal.

22. The system of claim 21, wherein the circuit components include at least one of a PIN diode or a parallel resonance tank circuit tuned to an MR frequency.

23. A system for an MRI diagnostic or interventional procedure, comprising:
a patient support table;
at least first and second hubs with a respective patch bay of between 12-200 connectors on the patient support table, with at least one of the hubs extending along at least one long side and/or foot end portion of the patient support table, wherein at least one connector and/or or at least one of the first and second patch bays has circuit components for one or more of RF decoupling, tuning and filtering signal and/or comprises a programmable switch;
a plurality of first leads extending from the first and second patch bay connectors, at least one that extends to at least one external patient sensor and at least one that extends to at least one intrabody device;
a plurality of second leads having opposing first and second ends, the first ends of the second leads connected directly or indirectly to the first and/or second patch bay in communication with a respective one or more of the first leads via the first and/or second patch bay, wherein the plurality of second leads are held in at least one cable bundle comprising a first cable bundle and the first cable bundle extends away from the patch bays with the second ends configured for attachment to remote components held in an adjacent control room through an RF shield associated with an MRI suite; and
a cable management system in communication with at least the first cable bundle, wherein the cable management system is configured to extend and retract at least the first cable bundle to provide an adjustable length of at least the first cable bundle in an MRI Scanner room of the MRI suite whereby at least the first cable bundle has substantially the same slack whether the patient support table is located inside or outside a magnet bore of an MRI Scanner in the MRI Scanner room due to longitudinal movement.

24. The system of claim 1, wherein the patient support table comprises a programmable switch with access via a top foot end portion of the patient support table.

25. The system of claim 1, wherein the patient support table provides a plurality of electrical paths of between 5-1000 from at least one patch bay on an end portion of the patient support table and the at least one patch bays to connect the first and second leads.

* * * * *

UNITED STATES PATENT AND TRADEMARK OFFICE
CERTIFICATE OF CORRECTION

Page 1 of 1

PATENT NO.          : 8,909,320 B2
APPLICATION NO.     : 12/708773
DATED               : December 9, 2014
INVENTOR(S)         : Jenkins et al.

It is certified that error appears in the above-identified patent and that said Letters Patent is hereby corrected as shown below:

In the Specification:
Column 9, Lines 30 and 31:
  Please correct "patent application Ser. Nos.112/090,583 and 12/090,583;"
          to read -- Patent Application Serial No. 12/090,583; --

In the Claims:
Column 16, Claim 12, Line 33: Please correct "a least the first"
          to read -- at least the first --

Signed and Sealed this
Twelfth Day of May, 2015

Michelle K. Lee
*Director of the United States Patent and Trademark Office*